(12) United States Patent
Ezzat et al.

(10) Patent No.: US 7,287,682 B1
(45) Date of Patent: Oct. 30, 2007

(54) SURGICAL DEVICE AND METHOD

(76) Inventors: Hazem Ezzat, 1494 Heatherwood, Troy, MI (US) 48098; M. Mounir Gazayerli, 1555 W. Big Beaver Rd., Bldg. G, Troy, MI (US) 48084; Gary L. Jones, 29151 Bannockburn, Farmington Hills, MI (US) 48334

( * ) Notice: Subject to any disclaimer, the term of this patent is extended or adjusted under 35 U.S.C. 154(b) by 603 days.

(21) Appl. No.: 10/366,170

(22) Filed: Feb. 13, 2003

Related U.S. Application Data (63) Continuation-in-part of application No. 10/348,087, filed on Jan. 20, 2003, now abandoned.

(51) Int. Cl.
*A61B 17/068* (2006.01)

(52) U.S. Cl. .................. 227/175.1; 606/142; 606/219; 227/176.1; 227/177.1; 227/180.1; 227/181.1

(58) Field of Classification Search ................ 606/138, 606/139, 142, 143, 219; 227/175.1, 175.2, 227/175.3, 176.1, 177.1, 178.1, 179.1, 181.1
See application file for complete search history.

(56) References Cited

U.S. PATENT DOCUMENTS

| | | | | |
|---|---|---|---|---|
| 4,550,870 A | * | 11/1985 | Krumme et al. ............... 227/19 |
| 5,433,721 A | * | 7/1995 | Hooven et al. ............. 606/143 |
| 5,529,235 A | * | 6/1996 | Boiarski et al. ......... 227/175.1 |
| 6,443,944 B1 | * | 9/2002 | Doshi et al. .................... 606/1 |
| 2004/0173659 A1 | * | 9/2004 | Green et al. ............. 227/176.1 |

* cited by examiner

*Primary Examiner*—(Jackie) Tan-Uyen Ho
*Assistant Examiner*—Darwin P. Erezo
(74) *Attorney, Agent, or Firm*—William J. Schramm, PC (57) ABSTRACT

A surgical device 20 for attaching staples 40 to a portion of a body comprising an anvil 23; a smart memory material (SMM) 50, 75 capable of going from one physical state to another physical state; a supply of staples in communication with the smart memory material and placed near the anvil; and an activating apparatus 21 which is in communication with the smart memory material and which can cause the change in the physical state of the smart memory material, which change in state causes the movement of the staples against the anvil thereby securing the staples 40 to the desired body portion. The device utilizes a source of electricity which when activated causes the SMM to expand in volume thereby moving an individual staple from the supply of staples. The device may also contain a surgical knife 62 to cut a body portion wherein a SMM is in communication with the knife whereby when the SMM expands it engages the knife causing the knife to cut the desired body portion.

34 Claims, 9 Drawing Sheets

SURGICAL DEVICE AND METHOD

CROSS-REFERENCE TO RELATED APPLICATION

This application is a continuation-in-part application to U.S. patent application Ser. No. 10/348,087 filed Jan. 20, 2003 now abandoned.

FIELD OF THE INVENTION

The invention pertains to a surgical device for attaching staples to a portion of a body. The invention also pertains to a surgical device for cutting a portion of a body.

The invention also pertains to smart memory materials that can change from one physical phase to another physical phase upon application of a stimulus and the use of those materials in a surgical device.

BACKGROUND OF THE INVENTION

Medical stapling devices for endoscopic or laparoscopic surgery employ very complex mechanisms. Frequently, the devices rely on a set of cam bars and the like to eject the surgical staples from the staple cartridge. (See U.S. Pat. No. 3,499,591.) Complex linkages contained within the body of the device are used to articulate the staple cartridge and an anvil into position during the surgical procedure. (See U.S. Pat. No. 6,250,532.) The range of motion, flexibility and size of such stapling devices are restricted by these mechanisms. Examples of complicated apparatus for applying surgical staples to attach an object to body tissue is described in U.S. Pat. Pub. 2002/0117534, published Aug. 29, 2002. The apparatus requires complex mechanical actuating mechanisms for rotating and articulating the surgical device and then to cause the staple to be ejected from a store of staples. A flexible connection (fire wire) with a high level of fatigue life is needed between the push rod and the pusher plate at the pivot point of the articulated joint. In a similar fashion, see U.S. Pat. No. 6,250,532. The devices described in the patents contain complex linkages to eject the staples from the staple cartridge/magazine limiting the range-of-motion for the articulated end of the device. In some of the devices, cam bars are used to deploy the staples. The ability of the cam bars to deflect or flex is limited to approximately +/−45' of movement. Additional, when operating at the extremes of this travel, early fatigue failure of the cam bars is possible.

The power required to actuate the device of the invention disclosed herein is supplied to the staple cartridge through very small and flexible wires. Because of the small size and flexibility, the required space and packaging requirements are significantly less in comparison to the cam bars described in the patents of the prior art.

Polymeric materials having smart memory characteristics are described in "Shape Memory Polymers": A. Yondlen, S. Kelch Angen, Chem Int. Ed. 2002, 41(12), pp. 2034-2057. The use of smart memory materials is discussed in U.S. Pat. No. 5,509,923. See also U.S. Pat. No. 6,388,043, herein incorporated by reference.

An apparatus for endoscopically applying body staples to body tissue is described in U.S. Pat. No. 5,484,095.

Other patents which are generally related to surgical devices or smart memory materials are recited below.

| PATENT NO./ PUBLICATION NO. | ISSUED/PUBLISHED APPL'N. DATE |
| --- | --- |
| U.S. Pat. No. 5,236,437* | Aug. 17,1993 |
| U.S. Pat. No. 5,242,458 | Sep. 7, 1993 |
| U.S. Pat. No. 5,411,519 | May 2, 1995 |
| U.S. Pat. No. 5,431,323* | Jul. 11, 1995 |
| U.S. Pat. No. 5,467,911 | Nov. 21, 1995 |
| U.S. Pat. No. 5,484,095 | Jan. 16, 1996 |
| U.S. Pat. No. 5,509,923 | Apr. 23, 1996 |
| U.S. Pat. No. 5,636,780 | Jun. 10, 1997 |
| U.S. Pat. No. 5,645,209 | Jul. 8, 1997 |
| U.S. Pat. No. 5,681,330 | Oct. 28, 1997 |
| U.S. Pat. No. 5,711,472 | Jan. 27, 1998 |
| U.S. Pat. No. 5,797,959 | Aug. 25, 1998 |
| U.S. Pat. No. 5,810,881 | Sep. 22, 1998 |
| U.S. Pat. No. 6,019,758 | Feb. 1, 2000 |
| U.S. Pat. No. 6,159,146 | Dec. 12, 2000 |
| U.S. Pat. No. 6,250,532 B1 | Jun. 26, 2001 |
| U.S. Pub. 2001/0007057 A1 | Pub. Jul. 5, 2001 |
| U.S. Pub. 2001/0030219 A1 | Pub. Oct. 18, 2001 |
| U.S. Pub. 2002/0072759 1 | Pub. Jun. 13, 2002 |
| U.S. Pub. 2002/0096550 1 | Pub. Jul. 25, 2002 |
| U.S. Pub. 2002/0117534 A1 | Pub. Aug. 29, 2002 |
| U.S. Pat. No. 6,488,196 B1 | Dec. 3, 2002 |

It is an object of the present invention to utilize a surgical device for attaching staples to a portion of a body by employing a smart memory material capable of going from one physical state to another physical state by means of an activating apparatus which is in communication with the smart memory material and which can cause the phase change which phase change causes movement of the staples against an anvil thereby securing the staples to the desired body portion.

It is also an object of the present invention to facilitate a method of attaching staples to a body portion utilizing the aforementioned surgical device.

It is also an object of the present invention to employ a surgical device for cutting a portion of a body where the surgical device has a knife that is capable of moving from a first to a second position which positions are spaced apart and to utilize a smart memory material which functions as described above; namely, utilizing an activating apparatus which is a communication with the smart memory material and by virtue of the change in the physical state can cause the movement of the knife thereby facilitating the cutting of the desired body portion.

It is also an object of the present invention to describe a method of performing a surgical operation employing the above-described surgical device for cutting a portion of the body.

It is also an object of the present invention to utilize the above-described surgical device for attaching staples which device also has the capability of cutting a portion of the body utilizing the combination of staples and knife by utilizing the combination of the surgical devices described above.

It is also an object of the present invention to perform a surgical operation utilizing the combined surgical device for stapling and cutting a portion of a body.

SUMMARY OF THE INVENTION

Described is a surgical device for attaching staples to a portion of a body comprising an anvil; a smart memory material (SMM) capable of going from one physical state to another physical state; a supply of staples in communication with the smart memory material and placed near the anvil; and an activating apparatus which is in communication with the smart memory material and which can cause the change in the physical state of the smart memory material, which change in state causes the movement of the staples against the anvil thereby securing the staples to the desired body portion.

The surgical device may also employ a knife for cutting a portion of a body comprising a knife capable of moving from a first position to a second position which is spaced apart from the first position; a smart memory material (SMM) capable of going from one physical state to another physical state; and an activating apparatus which is in communication with the smart memory material and which can cause the change in the physical state of the smart memory material, which change in state causes the movement of the knife thereby facilitating cutting of the desired body portion.

BRIEF DESCRIPTION OF THE DRAWINGS

An alternative embodiment of the invention is shown in FIGS. 13-15 and 17-19.

DETAILED DESCRIPTION OF THE INVENTION

Definitions:

Smart memory material (SMM) means a material or composition that can move from a first to a second physical state and then back to its desired original physical state by activation or stimuli. The change in state may result in an increase in volume of the SMM.

An "activating apparatus" means an apparatus that can stimulate the SMM thereby changing the state. The stimuli can be the application of heat and/or electrical current to SMM or some other mechanism that can effectuate the change in physical state. One example of physical state change is going from a martensite phase to an austenite phase.

The application of smart memory material can simplify a surgical stapling device into four basic components: a staple cartridge, an anvil for staple closure, an energy/power source (remote or local) and a switch/trigger (remote or local). The staple cartridge contains the surgical staple, a surgical blade and a SMM actuator/driver. The actuator/driver is used to drive the surgical staple from the cartridge, through the tissue and into contact with the anvil to initiate closure of the staples. The actuator/driver is also used to drive the surgical blade to create an incision in the tissue. The energy/power source is to supply the thermal energy or magnetic field to elicit a response of the smart materials actuator/driver and is triggered by the switch.

The flexibility of this concept provides several advantages over current devices as follows:

Staple actuator/driver can be located in the staple cartridge with staple

Surgical blade and actuator/driver may be incorporated in staple cartridge

Staple cartridge and anvil may be affixed to any device/handle for positioning during procedure Staple cartridge and anvil mechanism may be adapted to endoscopic or laparoscopic surgical procedures Staple cartridge is not limited in length by a mechanical actuation device The staple cartridge may be of various cross sections to fit the surgical application The surgical device may work with any form or size staple Staple cartridge may contain one, two, . . . to n staples in one, two, . . . n rows Staple cartridge may be configured to staple in linear, circular, concave, convex, parabolic or zigzag patterns, and the like The device facilitates driving individual staples from the staple cartridge sequentially, alternately and any combination thereof, and the like The device facilitates driving multiple staples or sets of staples in one operation The device facilitates driving sets of staples from a staple cartridge in a variety of configurations: single, multiple or alternating rows The device may be utilized to tack surgical incisions The surgical device herein is designed in such a way that it may be attached to any type of handle or device to articulate/manipulate its position and/or orientation. If the handle or device has the ability to articulate +/−180° (yaw) and rotate 360°, the desired development can be articulate through these extremes. This is possible because of the simplicity of the interface between the staple cartridge and the handle/device. The interface need only contain a method to hold the staple cartridge and an electrical connector. The electrical connector can be nothing more than electrical contains that are engaged by the staple cartridge when it is attached to the handle/device. The electrical connector is used to supply a voltage via small wires from the switch which is connected to the energy source. The electrical connector, integral to the staple cartridge, connects to the SMM contained in the cartridge to eject the staple when the voltage is supplied via the switch.

In the various embodiments, similar components use the same reference numerals.

Figure 1:
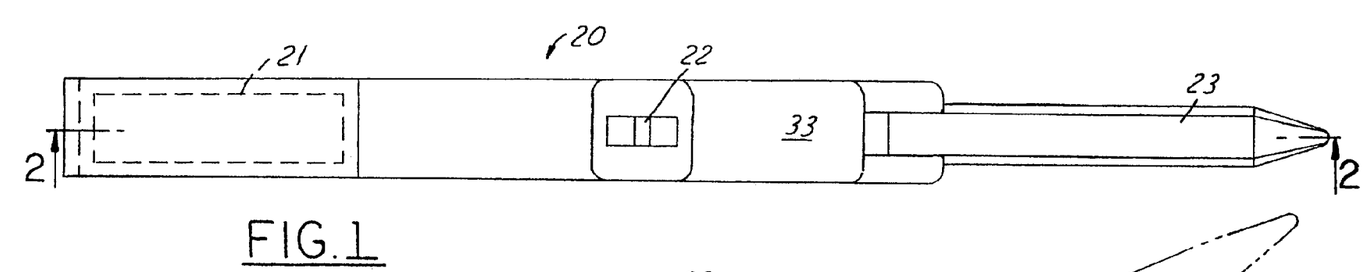
FIG. 1 is a top view of the surgical device of the present invention.
Figure 2:
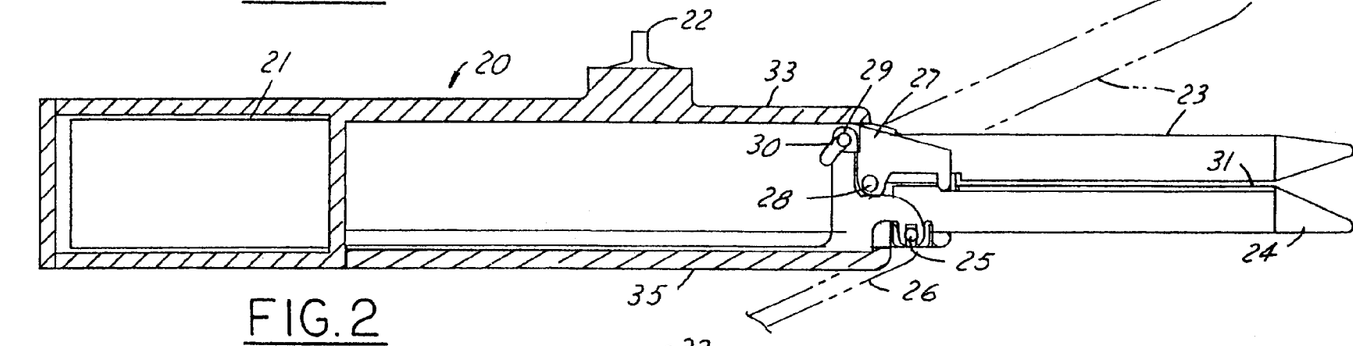
FIG. 2 is a side-sectional view of the surgical device of the present invention showing movement of the anvil in an open phantom view.

For a first embodiment FIGS. 1 and 2 show the top sectional and side cross section of one embodiment for a surgical (stapling) device 20. The surgical (stapling) device 20 has an energy source 21, contained in the body 27 of the device, a switch 22 that triggers the energy source, an anvil 23, a handle 26 to actuate the anvil 23 and a staple-actuator cartridge 24. There is also upper cover 33 and lower cover 35.

Figure 3:
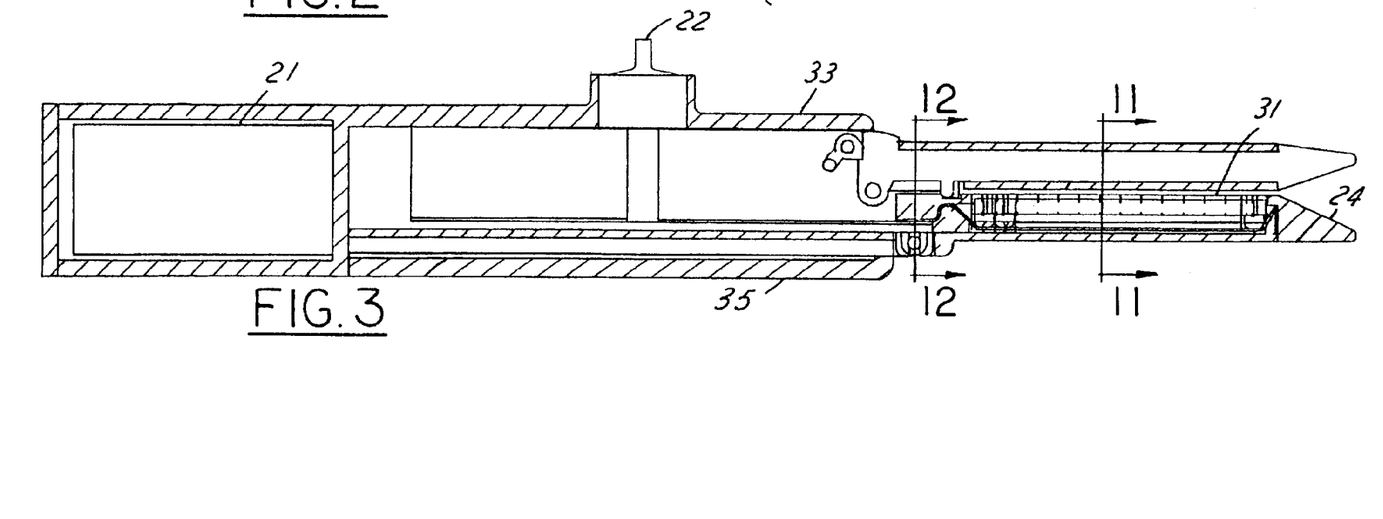
FIG. 3 is a side-sectional view of the surgical device of the present invention showing the smart memory material aligned with a store of staples.

The handle 26 is pivoted about pin 25. The anvil 23 pivots about pin 28 and is connected to the handle 26 by pin 29, which rides in a slot 30 in the body 27. As handle 26 is rotated from the opened (FIG. 2) to the closed position (FIGS. 1 and 3), the anvil 23 is then rotated from an open position to a closed position to clamp tissue (not shown) between the surface of the anvil 23 and the upper surface 31 of the staple-actuator cartridge 24.

The energy source 21, in a generic sense, is any source of power that initiates or elicits a response in a smart memory material. Examples are not limited to but include a voltage being applied directly to SMM to create a current that generates heat, a voltage being applied to a coil to generate heat or a magnetic field to stimulate the smart memory material. The energy source may also encompass any electrical, fluid, magnetic or chemical reaction that can be used to elicit a response from a smart memory material. The energy source may be a heating or cooling source.

Figure 6:
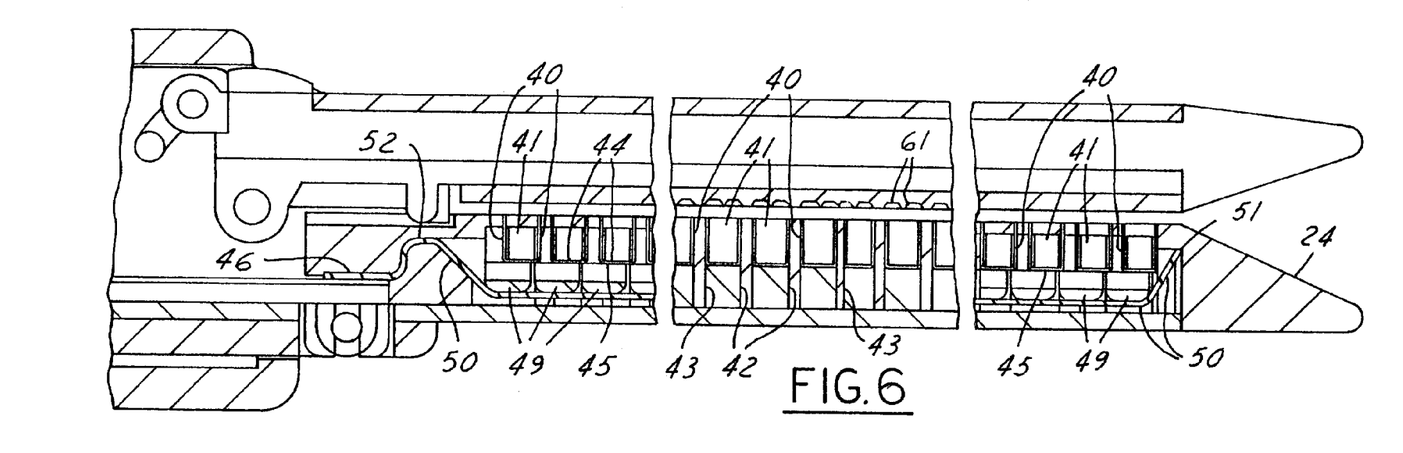
FIG. 6 is a side-sectional view of one embodiment of the surgical device of the present invention in the ready state.
Figure 6A:
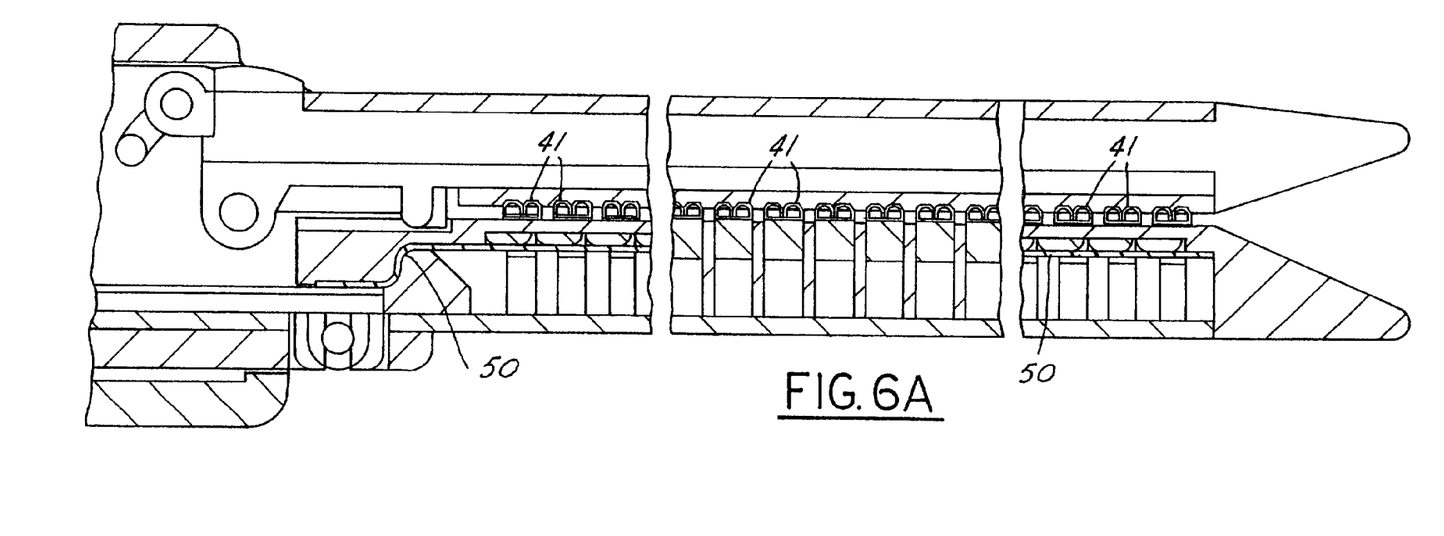
FIG. 6A is a side-sectional view of one embodiment in the engaged state; namely, the staples are secured towards the anvil.

In the staple-actuator cartridge 24, there is a plurality of staples 40 contained in a plurality of slots 41, as shown in FIGS. 6 and 6A. The plurality of staples 40 may be configured in single row or parallel rows (not shown). In the staple-actuator cartridge 24, a plurality of staples 40 are located in a plurality of slots 41 against the forward walls 42 and aft walls 43 of slots 41. The forward walls 42 and aft walls 43 act, as guides for staples 40 and pushers 49. The staples 40 are located in the downward position 44 against upper surface 45 of pushers 49. The plurality of pushers 49, is generally equivalent to the number of slots 41 and plurality of staples 40 having grooves in which a driver 50 is contained. The driver 50 is formed from smart memory material, for the embodiment shown in FIGS. 6, 6A and runs from the forward end 51 of the staple-actuator cartridge 24 to the aft end 52 of the staple-actuator cartridge 24. The SMM driver 50 is attached to the energy source 21 at connector 46.

Figure 4:
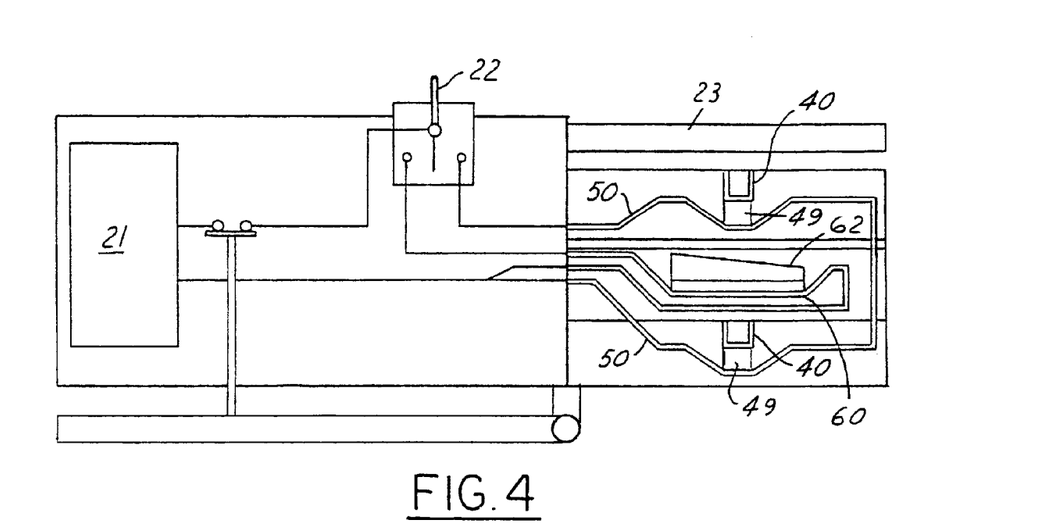
FIG. 4 is a schematic view of the surgical device of the present invention in a ready state.
Figure 5:
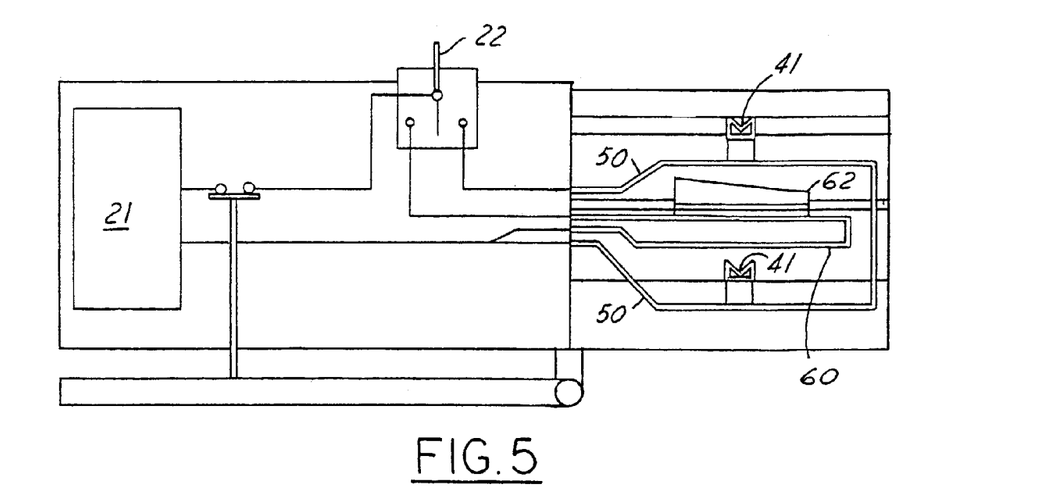
FIG. 5 is a schematic view of the surgical device of the present invention in an engaged state depicting the attachment of the staples and movement of the surgical knife.

FIGS. 4 and 5 show a block diagram for the control logic for the embodiment in FIGS. 6 and 6A.

When switch 22 is moved from the neutral position to the forward position, the energy source 21 will apply a voltage to the driver 50. The voltage in this instance can only be applied after the safety interlock(s) 51 are closed. As the voltage passes into driver 50, the resistance of the smart memory material will begin to generate heat. As the heat (energy) increases, the smart memory material will begin to go into a phase change such as from martensite to austenite. As this phase change occurs, driver 50 will begin to contract, causing the plurality of pushers 49 to move upward. As the plurality of pushers 49 move upward the plurality of staples 40 will begin to be ejected from the staple-actuator cartridge 24 and make contact with anvil 23. As driver 50 continues to contract, a force sufficient to completely drive the plurality staples 40 from the staple-actuator cartridge 24 and against anvil 23 to cause the plurality staples 40 to deform into their closed position 41 as shown in FIGS. 5 and 6A, securing the tissue (not shown). By closed position is meant that the legs of the staple are crimped, preferably together in slots 61 securely fastening the tissue to itself or to a mesh or substrate (not shown).

Figure 7:
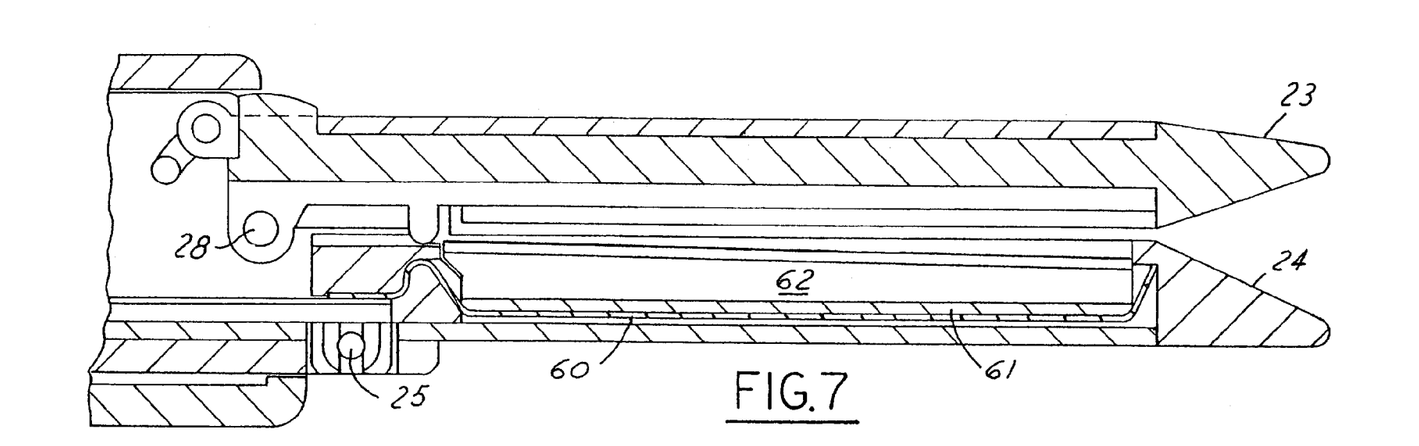
FIG. 7 is a side-sectional view of the surgical device of the present invention depicting the surgical knife in a recessed area.
Figure 8:
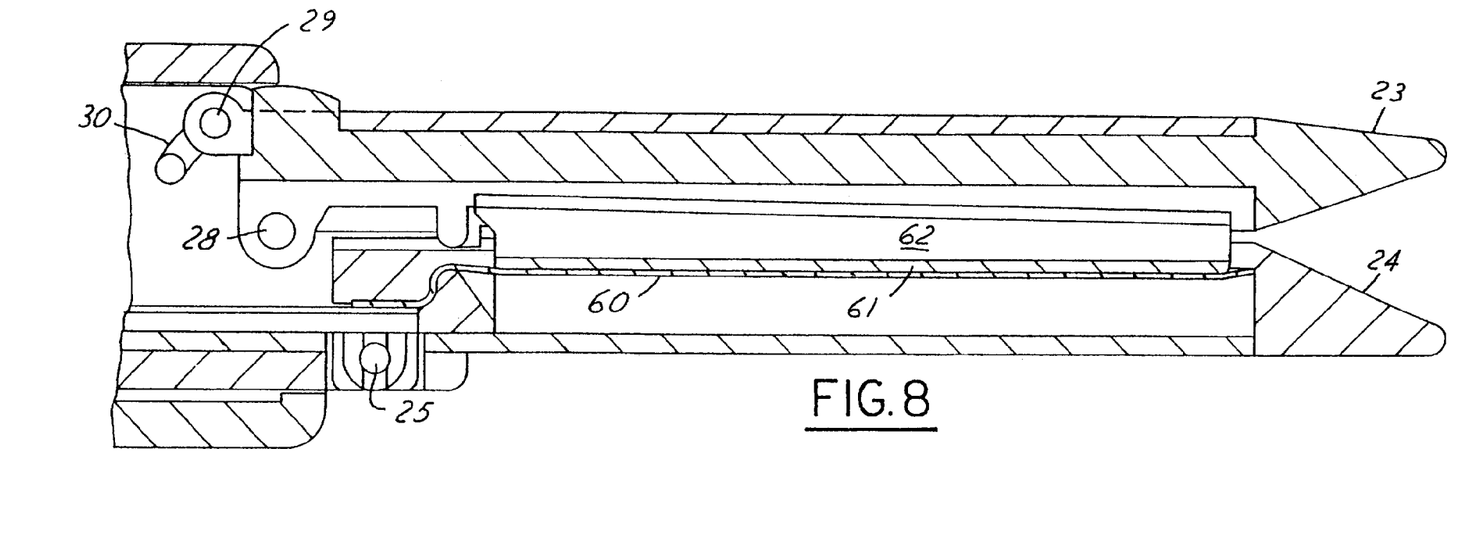
FIG. 8 is a side-sectional view of the surgical device of the present invention showing the surgical knife in an engaged position, out of the recessed area.

Contained in the staple-actuator cartridge 24, are driver 60, pusher 61 and surgical blade 62 as shown in FIGS. 5, 7 and 8. When switch 22 is moved from the forward position through the neutral position into the rearward position, the energy source 21 will apply a voltage to driver 60. The voltage in this instance preferably is applied after the safety interlock indicating completed staple ejection is closed. As the voltage passes into driver 60, the resistance of the smart memory material will begin to generate heat. As the heat (energy) increases, the smart memory material will begin to go into a phase change from martensite to austenite. As this phase change occurs, driver 60 will begin to contract, causing pusher 61 to move upward. As driver 60 continues to contract, sufficient force is generated to drive pusher 61 upward, in turn driving surgical blade 62 into its upward-most position as shown in FIG. 8. As the surgical blade 62 is driven upward, it can make an incision into the tissue between the rows of staples.

Figure 9:
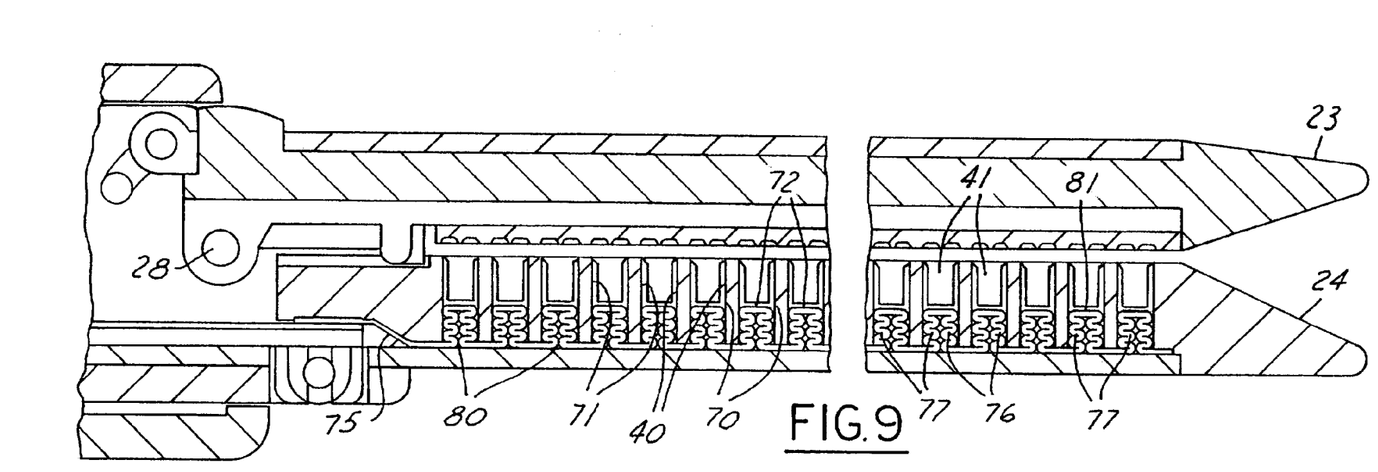
FIG. 9 is a side-sectional view of a second embodiment of the surgical device of the present invention in a ready state.
Figure 10:
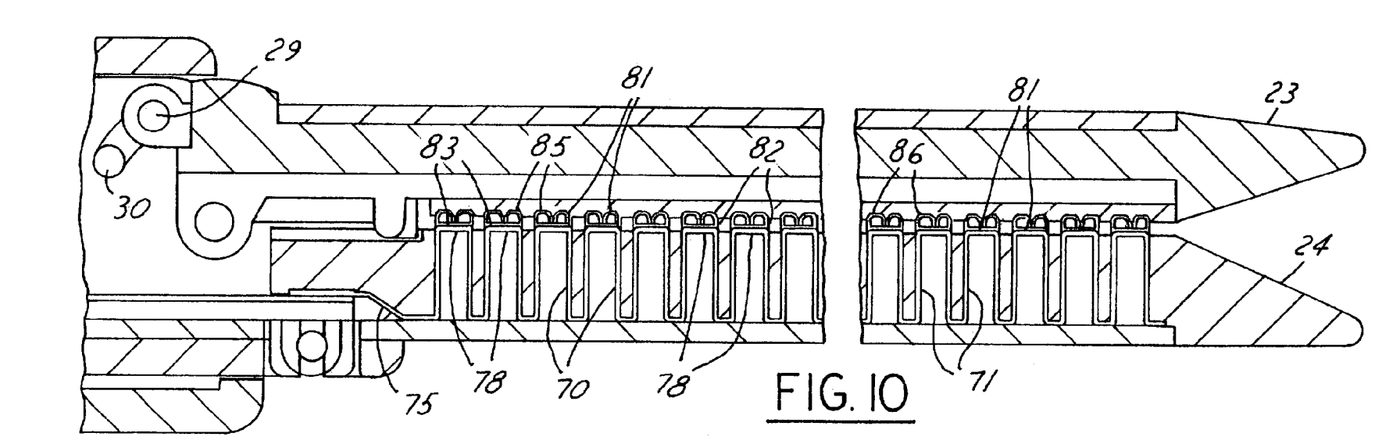
FIG. 10 is a side-sectional view of the second embodiment of the surgical device of the present invention in an engaged view with the staples secured.
Figure 11:
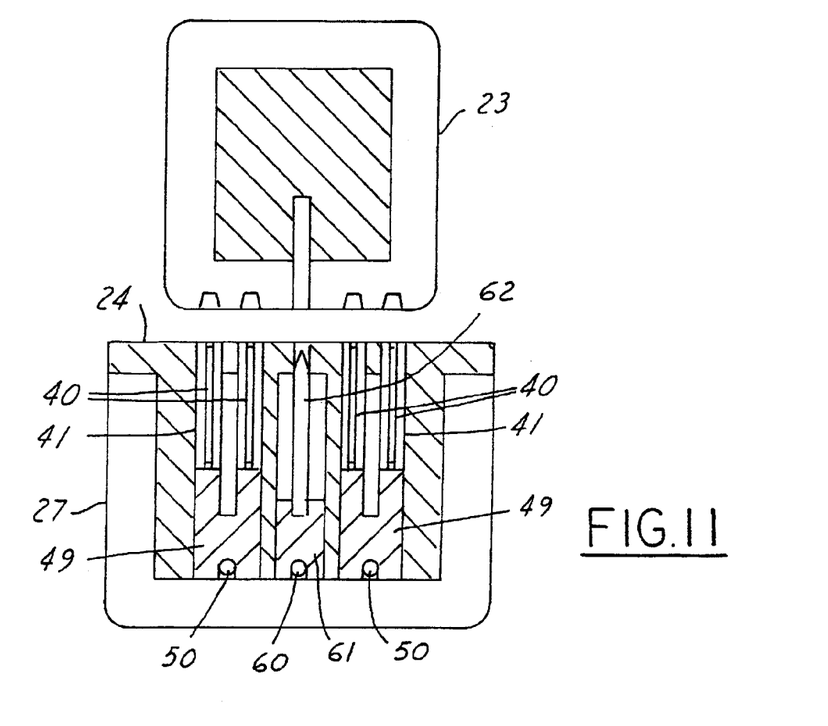
FIG. 11 is a sectional view through lines 11-11 of FIG. 3.
Figure 12:
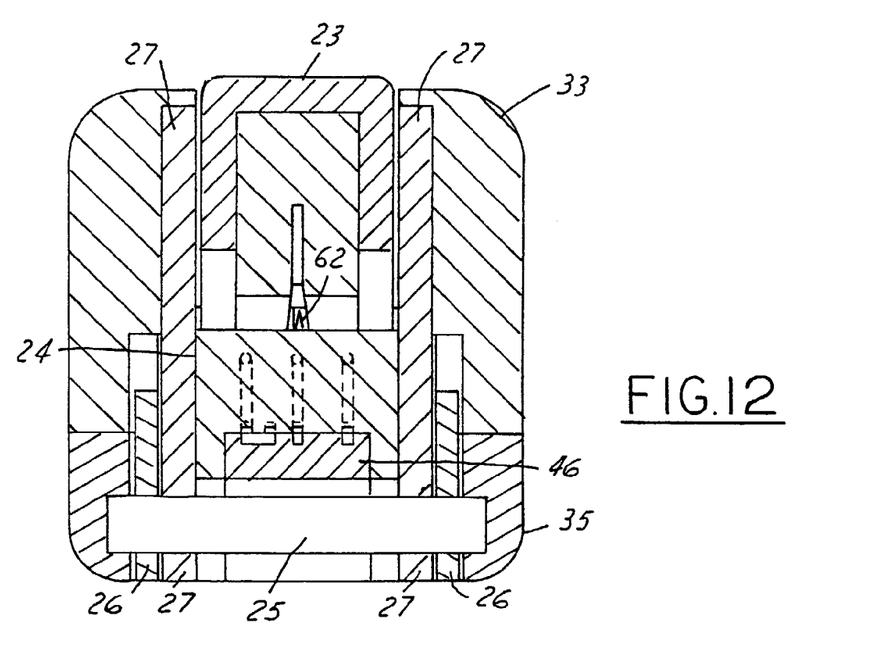
FIG. 12 is a sectional view along the lines 12-12 of FIG. 3.

An alternative embodiment is shown in FIGS. 9 and 10. In the staple-actuator cartridge 24, there is a plurality of staples 40 contained in a plurality of slots 41. From this point forward in this embodiment, the device will be described in the singular since for clarification.

In the staple-actuator cartridge 24, the staple 40 is located in slot 41 against the forward wall 70 and aft wall 71. Staple 40 is located in the downward position 72. The SMM driver 75 is folded in such a way as to form an "S" shaped forward leg, 76 and aft leg 77. The driver 75 is trapped between staple 40, the reaction surface 80, forward wall 70 and aft wall 71. When the energy source 21 applies a voltage (energy) to the driver 75, forward leg 76 and aft leg 77 will expand. As forward leg 76 and aft leg 77 expand, the upper segment (in the shape of a bar) 78 of the driver 75 reacts against the bottom leg 81 of staple 40 and reaction surface 80. As the forward leg 76 and aft leg 77 expand, the forward end 82 and aft end 83 of upper bar 78 are guided by the forward wall 70 and aft wall 71 of staple-actuator cartridge 24. As the forward leg 76 and aft leg 77 expand, the staple 40 is moved linearly until it contacts the surface of the anvil 23 to initiate closure of the staple 40. The forward leg 76 and aft leg 77 expand until staple 40 is ejected from staple-actuator cartridge 24 and forward staple leg 85 and aft staple leg 86 are fully closed or crimped as shown in FIG. 10, securing the tissue and/or mesh or substrate (not shown).

The surgical stapling device can be configured to eject the staples from the staple-actuator cartridge individually or in any combination. A solid-state logic controller in the stapling device handle can facilitate this feature which one of ordinary skill in the art can assemble.

It is to be appreciated that the staple-actuator cartridge is not limited to linear forms. Because of the flexibility of the smart material (i.e., shape memory alloys and shape memory polymers), the staple-actuator cartridge can take on any form: circular, concave, convex, parabolic, zigzag or the like. The cross sectional shape of the staple-actuator cartridge can also be tailored to meet the surgical need.

Figure 13:
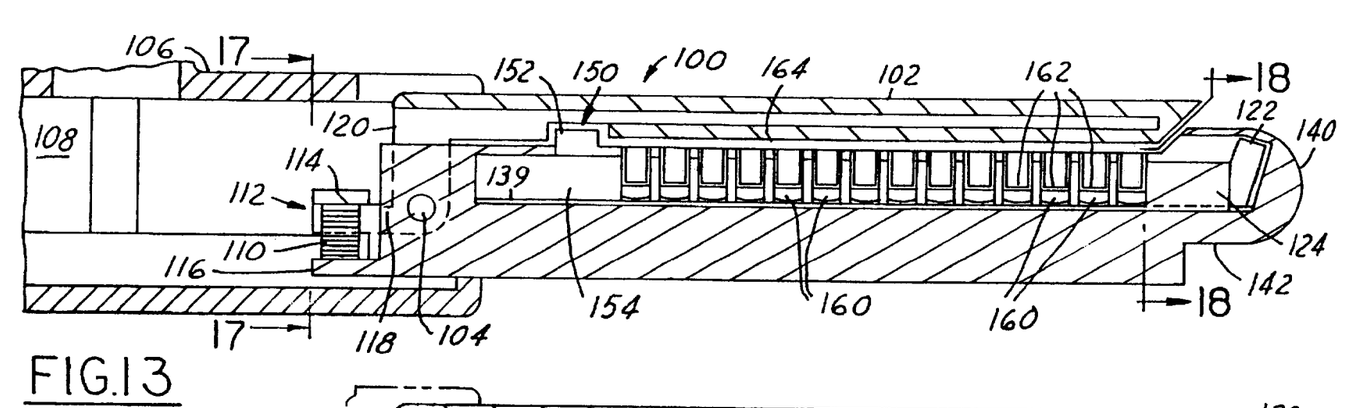
FIG. 13 is a side-sectional view of an alternative embodiment of the present invention.
Figure 14:
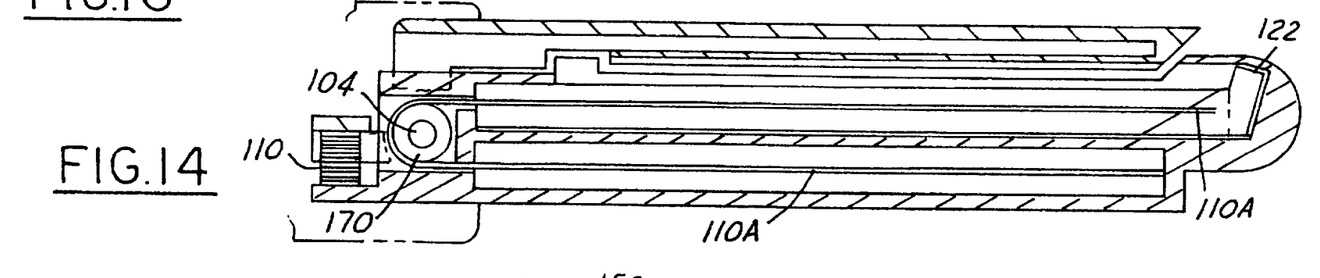
FIG. 14 is a side-sectional view of an alternative embodiment of the present invention wherein the surgical knife is in a first position prior to a surgical cutting operation.
Figure 15:
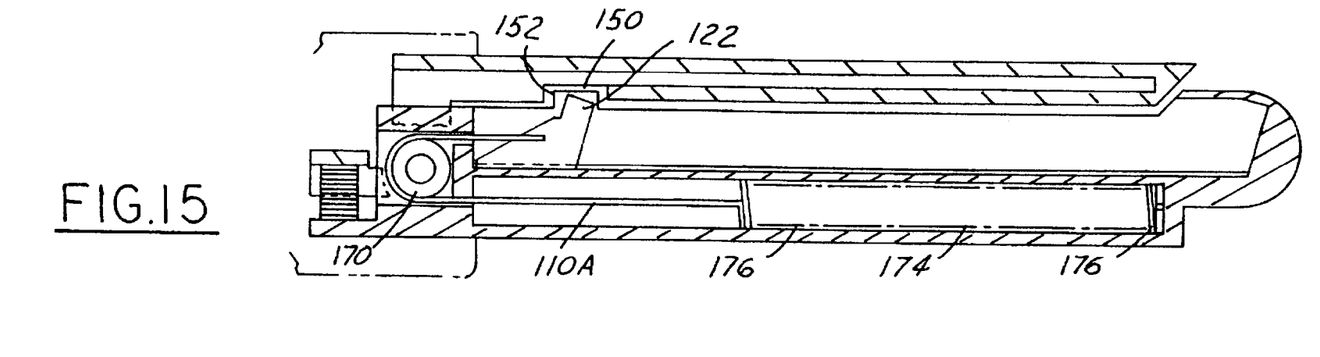
FIG. 15 is a side-sectional view of an alternative embodiment of the present invention wherein the surgical knife is in a second position from the first position of FIG. 14 wherein the surgical knife has moved from the first position to the second position.

Another embodiment of the present invention is that depicted in FIGS. 13-15.

The surgical device 100 has handle 106 and anvil 102. The device contains the energy source 108 which is connected to the SMM material 110 retained within assembly 112 having a top portion 114 and a bottom portion 116. The anvil 102 has an extension portion 118 that is engagement with the SMM material 110. As the SMM material moves, the anvil 102 moves upward when viewing FIG. 13 causing arm 120 to rotate upward.

Figure 19:
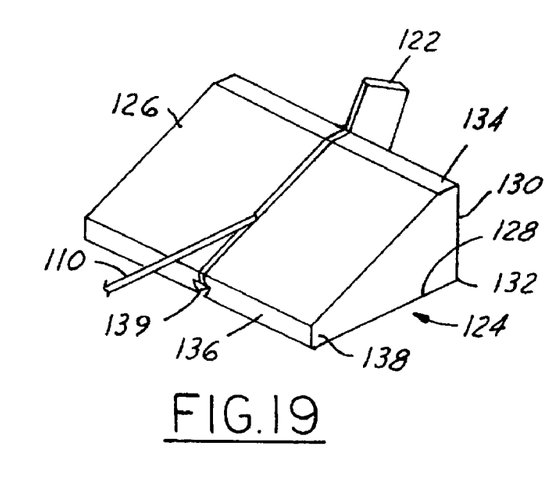
FIG. 19 is a perspective view of a wedge with surgical knife utilized in the present invention.

In the embodiment depicted in FIG. 13, a surgical blade 122 is attached to or a portion of a wedge 124 (best shown in FIG. 19) which has attached thereto the SMM material 110. The wedge has angled surface 126 to indicate the initiation of action. The wedge has a bottom surface 128 and a back side surface 130 which forms approximately a 90° angle at their juncture 132. The wedge 124 has a top portion 134, a front portion 136 and side 138. Side 138 as can be seen from FIG. 19 is substantially smaller than back side portion 130 reflecting the angled surface 126 from the back portion 134 to the front surface 136. The wedge 124 has a groove 139 which rides a "T" shaped track. The wedge slides on the track during the cutting operation of the blade. In a resting or first position, the blade 122 is positioned at the front portion 140 of the surgical device which may take any configuration but is shown as a semicircular configuration for ease of insertion into the body portion for ease of handling during a clinical operation. The surgical device 100 has a bottom portion 142. The SMM material 110 can be secured to the wedge 124 by any convenient mechanism such as by adhesion and the like, with or without the use of heat or other securing method.

Figure 17:
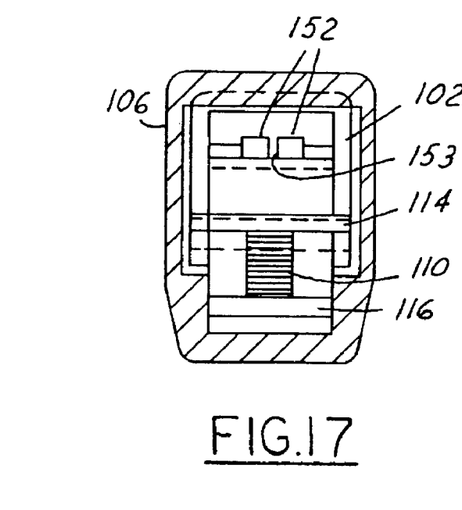
FIG. 17 is a sectional view taken along the lines 17-17 of FIG. 13.
Figure 18:
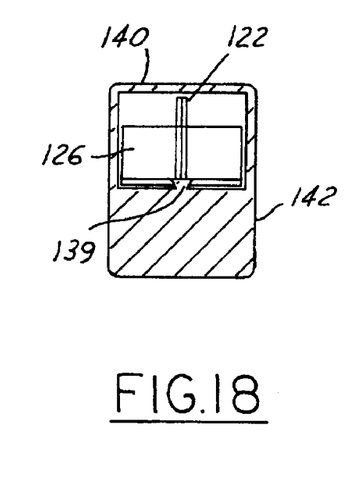
FIG. 18 is a sectional view taken along the lines 18-18 of FIG. 13.

The surgical device 100 has a wedge receiving section 150 in which top portion 152 receives the blade 122 and bottom portion 154 which receives wedge segment 124. The blade receiving slot 153 is shown in FIG. 17.

As the wedge 124 moves from the position on the right as shown in FIG. 13 to the end section 150, the front portion of the wedge surfaces 136 & 126 initiation movement against pushers 160 and therefore against the staples 162 and against the bottom surface 164 of the anvil thereby engaging body tissue. After the staples engage the tissue, the blade 122 will cut the tissue.

FIGS. 14 and 15 are further details of the surgical device of FIG. 13. FIG. 14 indicates that the surgical knife 122 is on the right portion of the apparatus of the surgical device where the SMM material 110A is circled about pulley 170 which rotates about pivot point 104. The surgical knife moves from the right to the left as shown in FIG. 15 where the surgical knife 122 fits into the receiving segment 152. As the surgical knife moves from the right to the left portion of the surgical device, the SMM material 110A goes from a linear position as shown in FIG. 14 to a curled position 174 in FIG. 15. In other words, by the application of heat the SMM material goes from a linear mode as depicted in FIG. 14 into a more curled position where the curl is in segment 176 of the FIG. 15. The operation of FIGS. 13-15 indicates that one SMM material 110 operates the anvil to an open or closed position. Another or different SMM material 110A activates the movement of the surgical knife from the right portion of FIG. 14 to the left portion of FIG. 15. While it is expected that these would be two separate operable SMM materials, it is obvious to one of skill in the art that the materials can be lengthened and there could be separate segments that would have the ability to operate both actions namely the movement of the anvil and the movement of the blade. For convenience, the electrical connections of FIGS. 13-15 are not supplied in detail but would be clear to one of skill in the art.

Figure 16:
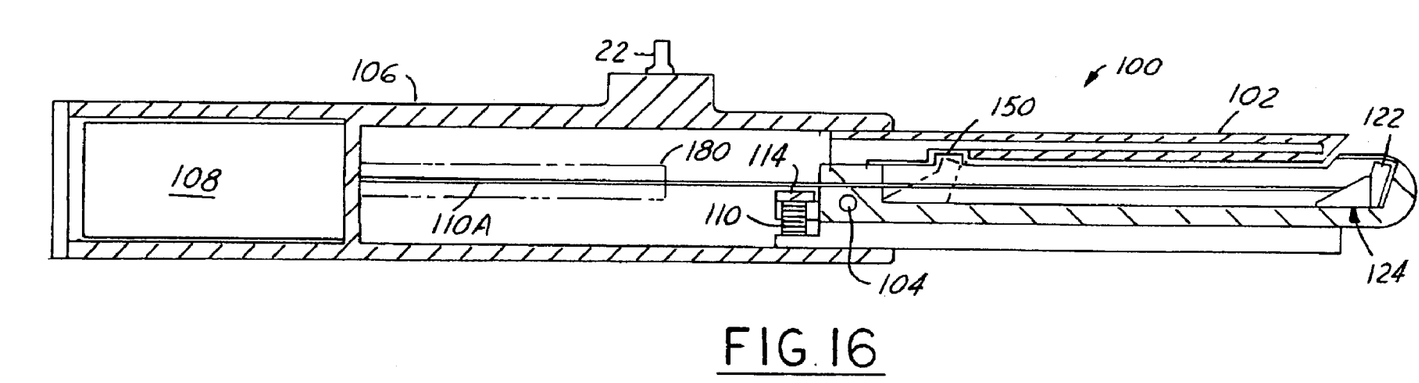
FIG. 16 is another embodiment of the invention.

FIG. 16 is a schematic view of another alternative of the present invention. The surgical device 100 of FIG. 16 is an alternative embodiment of the operation of the wedge 124 and surgical knife 122. In FIG. 16, the heating mechanism 108 is attached to the SMM 110A. The embodiment shown in FIG. 16, however, does not have the pulley arrangement as shown in FIG. 15. In the embodiment of FIG. 16, the surgical knife moves from the right portion of the surgical device 100 to the left portion of the surgical device stopping at receiving position 150. The action of the SMM is primarily retained in the horizontal plane of the surgical device 100 without the SMM going around a pulley. In the embodiment of FIG. 16, the SMM is primarily in a linearly fashion and during the movement from one phase to another. The SMM can collect in a retaining box 180 in FIG. 16.

FIGS. 20A-D depict an alternative embodiment of the wedge with surgical knife utilized in the present invention.

Figures 20A, 20B, 20C, 20D:
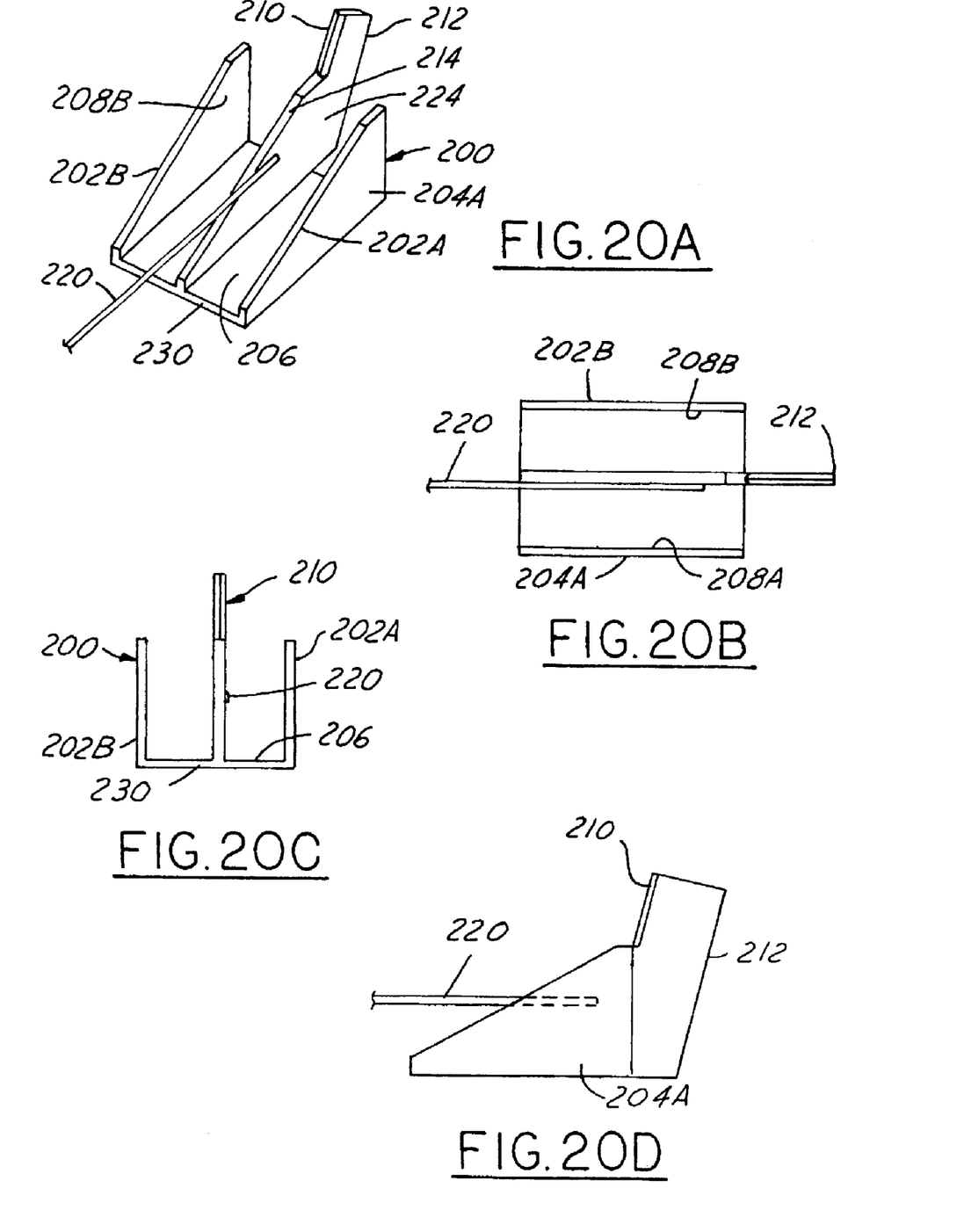
FIGS. 20A-D depict an alternative embodiment of the wedge with surgical knife utilized in the present invention.

The wedge 200 is comprised of sloping surfaces 202A and 202B. FIG. 20A is a perspective view of the wedge utilized in the present invention. FIG. 20B is a top view of FIG. 20A. FIG. 20C is a front view of FIG. 20A and FIG. 20D is a side view of FIG. 20A showing the attachment of the SMM to the interior portion of the wedge.

The wedge has exterior side surfaces 204A and 204B, bottom surface 206 and interior surface 224. The surgical knife has a cutting edge 210 and a back portion 212. Extension 214 of the blade likewise is angled for movement of the wedge when it comes in contact with the pushers for movement of the staples. The angle for surface 214 is comparable to that for surfaces 202A and B. The SMM 220 is attached to the interior surface 224 of the extension 214 of the surgical knife. The wedge 200 has a front lip 230.

It is to be appreciated that the surgical device utilizing its smart memory material need not utilize the knife portion. In that case, the stapling device can operate as described herein. Alternatively, the surgical device need not utilize the staple portion. In which case the knife portion may be utilized as described herein. Preferably, however, the knife and stapling mechanism are utilized together as shown.

The driver for ejecting the staples from the staple-actuator cartridge is not limited to smart memory alloy materials. A smart memory polymer can also provide the actuating force and displacement. Some smart memory materials include Nitinol (an acronym for Nickel Titanium Naval Ordnance Laboratory) which is a family of intermetallic materials, which contain a nearly equal mixture of nickel (about 55 wt. %) and titanium. Some of those alloy compositions are superelastic materials such as alloy N, S and C and others are actuator materials, such as alloy B, M, H and Flexinol (trademark of Nitinol Devices and Components for nickel titanium intermetallic alloys).

Nitinol exhibits unique behavior. The two terms used to describe this behavior are "Shape Memory" and "Superelasticity".

SHAPE MEMORY: Shape memory effect describes the process of restoring the original shape of a plastically deformed sample by heating it. This is a result of a crystalline phase change known as "thermoelastic martensitic transformation". Below the transformation temperature, Nitinol is martensitic. The soft martensitic microstructure is characterized by "self-accommodating twins", a zigzag like arrangement. Martensite is easily deformed by de-twinning. Heating the material converts the material to its high strength, austenitic condition. The transformation from austenite to martensite (cooling) and the reverse cycle from martensite to austenite (heating) do not occur at the same temperature. There is a hysteresis curve for every Nitinol alloy that defines the complete transformation cycle. The shape memory effect is repeatable and can typically result in up to 8% strain recovery.

SUPERELASTICITY: Martensite in Nitinol can be stress induced if stress is applied in the temperature range above Af (austenite finish temperature). Less energy is needed to stress-induce and deform martensite than to deform the austenite by conventional mechanisms. Up to 8% strain can be typically accommodated by this process. Since austenite is the stable phase at this temperature under no-load conditions, the material springs back to its original shape when the stress is removed. This extraordinary elasticity is also called "pseudoelasticity" or transformational "superelasticity". The typical stress-strain curve of a properly processed Nitinol alloy shows the loading and unloading plateaus, recoverable strain available, and the dependence of the loading plateau on the ambient temperature as is well known in the art. The loading plateau increases with the ambient temperature. As the material warms above the austenite finish temperature, the distinctive superelastic "flag" curve is evident. Upon cooling, the material displays less elasticity and more deformation until it is cooled to where it is fully martensite; hence, exhibiting the shape memory property and recovering its deformation upon heating. Nitinol alloys are superelastic in a temperature range of approximately 50 degrees above the austenite finish temperature. Alloy composition, material processing, and ambient temperature greatly effect the superelastic properties of the material. For medical devices binary Nitinol alloys, when processed correctly, are at their optimum superelastic behavior at body temperature.

Nitinol Devices & Components manufactures binary Nitinol materials with Afs ranging from −15 degrees centigrade to +100 degrees centigrade for both superelastic and shape memory applications.

Smart memory materials can also be metallic alloys of copper, zinc and aluminum or iron, nickel and aluminum, and the like.

Many modifications and variations of the present invention are possible in light of the above teachings. Therefore, it is to be understood that within the scope of the appended claims, the inventions may be practiced otherwise than as specifically described. For example, numerous mechanisms may be available for articulating and modifying the size and configuration of the surgical device. Moreover, the reference numerals are merely for convenience and are not intended to be in any way limiting. Similarly, the components of the invention can be arranged relative to one another in a variety of configurations other than those shown.

The invention claimed is:

1. A surgical device for attaching staples to a body portion comprising:
   a first and second jaws for receiving said body portion there between;
   the first jaw comprising an anvil in communication with a first smart memory material for facilitating the opening and closing of the first jaw towards the second jaw, wherein the first smart memory material is capable of moving from a first physical state in which the first and second jaws are in an open position and a second physical state in which the first and second jaws are in a closed position;
   the second jaw comprising a supply of staples in communication with a second smart memory material for deploying the supply of staples towards the anvil and piercing the body portion located there between, wherein the second smart memory material is capable of moving from a first physical state in which the supply of staples are in an undeployed state and a second physical state in which the supply of staples are deployed towards the anvil; and
   an activating apparatus in communication with the smart memory materials for causing the first and second smart memory materials to change from their respective first physical state to their respective second physical state.

2. The surgical device of claim 1 wherein the first or second smart memory material is a metallic alloy.

3. The surgical device of claim 1 wherein the first or second smart memory material is a polymeric material.

4. The surgical device of claim 1 wherein the activating apparatus is a source of electricity which when activated causes the second smart memory material to expand in volume thereby moving an individual staple from the supply of staples.

5. The surgical device of claim 1 wherein the activating apparatus causes the second smart memory material to expand in volume thereby moving an individual staple from the supply of staples.

6. The surgical device of claim 1 further comprising a surgical knife to cut a desired body portion.

7. The surgical device of claim 1 further comprising a surgical knife to cut a desired body portion wherein a third smart memory material is in communication with the knife whereby when the third smart memory material expands it engages the knife causing the knife to cut the desired body portion.

8. The surgical device of claim 1 wherein the first or second smart memory material is a metallic alloy comprised of a composition, which can go from a martensite phase to an austenite phase.

9. The surgical device of claim 1 wherein the first or second smart memory material is a metallic alloy comprised of copper, zinc and aluminum or iron, nickel and aluminum.

10. The surgical device of claim 1 wherein the first or second smart memory material is a metallic alloy comprised of nickel and titanium.

11. The surgical device of claim 1 wherein the second smart memory material is in communication with a pusher which engages a staple in the movement of the staple towards the anvil.

12. The surgical device of claim 1 wherein a third smart memory material is in engagement with a wedge segment containing a surgical knife such that the change in physical state of the third smart memory material will cause movement of the wedge.

13. A method of securing a portion of a body comprising:
providing the device of claim 12; and
securing the staples to the desired body portion.

14. The surgical device of claim 12 wherein the second smart memory material causes movement of the staples against the anvil and the third smart memory material causes movement of the surgical knife to cut a desired body part.

15. A method of securing a portion of a body comprising:
providing the device of claim 14; and
securing the staples to the desired body portion.

16. The surgical device of claim 1 wherein the second smart memory material is attached to a moving wedge which causes movement of the staples against the anvil and wherein the second smart memory material rotates about a pivot point during the movement of the wedge to engage the staples.

17. A method of securing a portion of a body comprising:
providing the device of claim 16; and
securing the staples to the desired body portion.

18. The surgical device of claim 1 wherein a third smart memory material is attached to a wedge having a surgical knife portion capable of moving from a first position to a second position and wherein the third smart memory material which causes movement of the wedge is in substantially a horizontal position at the beginning and at the end of the movement of the wedge.

19. A method of securing a portion of a body comprising:
providing the device of claim 18; and
securing the staples to the desired body portion.

20. A method of securing a portion of a body comprising:
providing the device of claim 1; and
securing the staples to the desired body portion.

21. The method of claim 20 wherein the first or second smart memory material is a metallic alloy.

22. The method of claim 20 wherein the first or second smart memory material is a polymeric material.

23. The method of claim 20 wherein the activating apparatus is a source of electricity which when activated causes the second smart memory material to expand in volume thereby moving an individual staple from the supply of staples.

24. The method of claim 20 wherein the activating apparatus causes the second smart memory material to expand in volume thereby moving an individual staple from the supply of staples.

25. The method of claim 20 further comprising a surgical knife to cut a desired body portion.

26. The method of claim 20 further comprising a surgical knife to cut a desired body portion wherein a third smart memory material is in communication with the knife whereby when the third smart memory material expands it engages the knife causing the knife to cut the desired body portion.

27. The method of claim 26 wherein the first, second or third smart memory material is a metallic alloy.

28. The method of claim 26 wherein the first, second or third smart memory material is a polymeric material.

29. The method of claim 26 wherein the first, second or third smart memory material is a metallic alloy comprised of a composition, which can go from a martensite phase to an austenite phase.

30. The method of claim 26 wherein the first, second or third smart memory material is a metallic alloy of copper, zinc and aluminum or iron, nickel and aluminum.

31. The method of claim 26 wherein the first, second or third smart memory material is a metallic alloy comprised of nickel and titanium.

32. The method of claim 20 wherein the first or second smart memory material is a metallic alloy comprised of a composition, which can go from a martensite phase to an austenite phase.

33. The method of claim 32 wherein the first or second smart memory material is a metallic alloy of copper, zinc and aluminum or iron, nickel and aluminum.

34. The method of claim 33 wherein the first or second smart memory material is a metallic alloy comprised of nickel and titanium.

* * * * *